United States Patent
Inoue et al.

(10) Patent No.: US 12,412,266 B2
(45) Date of Patent: Sep. 9, 2025

(54) INFORMATION PROCESSING DEVICE, SCREENING DEVICE, INFORMATION PROCESSING METHOD, SCREENING METHOD, AND PROGRAM

(71) Applicant: Kyoto University, Kyoto (JP)

(72) Inventors: Haruhisa Inoue, Kyoto (JP); Keiko Imamura, Kyoto (JP); Yuichiro Yada, Kyoto (JP)

(73) Assignee: Kyoto University, Kyoto (JP)

( * ) Notice: Subject to any disclaimer, the term of this patent is extended or adjusted under 35 U.S.C. 154(b) by 694 days.

(21) Appl. No.: 17/614,243

(22) PCT Filed: May 29, 2020

(86) PCT No.: PCT/JP2020/021384
§ 371 (c)(1),
(2) Date: Nov. 24, 2021

(87) PCT Pub. No.: WO2020/241836
PCT Pub. Date: Dec. 3, 2020

(65) Prior Publication Data
US 2022/0215544 A1 Jul. 7, 2022

(30) Foreign Application Priority Data
May 31, 2019 (JP) .................. 2019-103294

(51) Int. Cl.
*G06T 7/00* (2017.01)
*G16H 50/20* (2018.01)

(52) U.S. Cl.
CPC .......... *G06T 7/0012* (2013.01); *G16H 50/20* (2018.01); *G06T 2207/10056* (2013.01); *G06T 2207/20081* (2013.01); *G06T 2207/30024* (2013.01)

(58) Field of Classification Search
CPC ......... G06T 7/0012; G06T 2207/30024; G06T 2207/30016; G06T 2207/20081;
(Continued)

(56) References Cited

U.S. PATENT DOCUMENTS 7,711,174 B2 * 5/2010 Sammak ............... G06T 7/0012
424/278.1
9,097,727 B2 8/2015 Inque et al.
(Continued)

FOREIGN PATENT DOCUMENTS

JP 2013520960 6/2013
JP 2018045559 3/2018
(Continued)

OTHER PUBLICATIONS

Aggeliki Vlachostergiou et al., "Multi-Task Learning for Predicting Parkinson's Disease Based on Medical Imaging Information," 2018 25th IEEE International Conference on Image Processing (ICIP), Athens, Greece, 2018, pp. 2052-2056, doi: 10.1109/ICIP.2018.8451398. (Year: 2018).*
(Continued)

*Primary Examiner* — Manav Seth
(74) *Attorney, Agent, or Firm* — Dority & Manning, P.A.

(57) ABSTRACT

An information processing device includes: an acquirer configured to acquire images obtained by imaging cells differentiated from pluripotent stem cells derived from a subject; and a predictor configured to input the images acquired by the acquirer to a model trained on data in which information indicating at least an intractable neurological disease is associated with an image obtained by imaging the cells of the intractable neurological disease differentiated from the pluripotent stem cells, and predict an onset of the intractable neurological disease of the subject based on output results of the model to which the images were input.

15 Claims, 13 Drawing Sheets

(58) Field of Classification Search
CPC .......... G06T 2207/10056; G06T 2207/20084;
G16H 30/40; G16H 50/30; G16H 10/40;
G16H 50/70; G16H 30/20; G16H 50/20;
G06V 20/69; G06V 20/698; G06V 10/82;
G06V 10/70; G06V 10/774–7796; A61B
5/4076; A61B 5/4082; A61B 5/4088;
G01N 2800/2821; G01N 33/6896; G01N
2015/1488; G01N 2015/1402; G01N
15/1459; G01N 33/6893; G01N 33/5044;
G01N 2800/2878; G01N 2333/96486;
G01N 33/5308; G06N 3/0464; G06N
3/084; G06N 3/09; G06N 3/02–126;
G06N 20/00–20; G06N 3/088; G06N
3/094; G06F 18/214–2155; G06F 7/023;
G06F 40/16

See application file for complete search history.

(56) References Cited

U.S. PATENT DOCUMENTS

| | | | | |
|---|---|---|---|---|
| 10,249,389 | B2* | 4/2019 | Athey | G16H 50/30 |
| 11,037,292 | B2* | 6/2021 | Wakui | G01N 21/27 |
| 2006/0039593 | A1* | 2/2006 | Sammak | G06V 10/764 382/160 |
| 2013/0034858 | A1* | 2/2013 | Inoue | G01N 33/6896 435/7.1 |
| 2015/0301028 | A1* | 10/2015 | Eggan | G01N 33/5023 435/29 |
| 2015/0301030 | A1* | 10/2015 | Eggan | G01N 33/5023 435/29 |
| 2016/0186146 | A1 | 6/2016 | Thomson et al. | |
| 2018/0082215 | A1 | 3/2018 | Mizobuchi | |
| 2022/0028488 | A1* | 1/2022 | Rubin | G16H 10/40 |
| 2022/0215543 | A1* | 7/2022 | Inoue | G16H 30/40 |

FOREIGN PATENT DOCUMENTS

| | | | |
|---|---|---|---|
| WO | WO2011108766 | 9/2011 | |
| WO | WO-2011047103 A3 * | 11/2011 | ........... G06V 10/764 |
| WO | WO2016144838 | 9/2016 | |
| WO | WO2017022854 | 2/2017 | |
| WO | WO2017136285 | 8/2017 | |
| WO | WO2018211687 | 11/2018 | |
| WO | WO2018216705 | 11/2018 | |
| WO | WO-2020118158 A1 * | 6/2020 | ........... C12N 5/0696 |

OTHER PUBLICATIONS

Yichen Shi et al., "A Human Stem Cell Model of Early Alzheimer's Disease Pathology in Down Syndrome". Sci. Transl. Med.4, 124ra29-124ra29(2012).DOI:10.1126/scitranslmed.3003771 (Year: 2012).*
Yoichi Imaizumi et al., "Modeling human neurological disorders with induced pluripotent stem cells,"J. Neurochem. (2014) 129, 388-399, doi: 10.1111/jnc.12625 (Year: 2014).*
Witmer et al., 2018, "Multi-label Classification of Stem Cell Microscopy Images using Deep Learning" (pp. 1408-1413). (Year: 2018).*
Waisman et al., Apr. 9, 2019, "Deep Learning Neural Networks Highly Predict Very Early Onset of Pluripotent Stem Cell Differentiation" (pp. 845-859) (Year: 2019).*
Kusumoto et al., 2018, "Automated Deep Learning-Based System to Identify Endothelial Cells Derived from Induced Pluripotent Stem Cells" (pp. 1687-1695) (Year: 2018).*
Fan et al., 2017, "A Machine Learning Assisted, Label-free, Non-invasive Approach for Somatic Reprogramming in Induced Pluripotent Stem Cell" (pp. 1-9). (Year: 2017).*
Eric M. Christiansen et al., In silico labeling: Predicting fluorescent labels in unlabeled images, Cell. Apr. 19, 2018; 173(3): 792-803.
Nicolas Coudray et al., Classification and mutation prediction from non-small cell lung cancer histopathology images using deep learning, Nature Medicine, vol. 24, Oct. 2018, 1559-1567.
T. Kondo et al., 15. Therapeutic application of iPS cells, Nihon Naika Gakkai Zasshi, 2013, vol. 102, No. 8, pp. 2015-2022.
PCT International Search Report for PCT/JP2020/021384, mailed Aug. 18, 2020.
Centeno, E. G. Z. et al., "2D versus 3D human induced pluripotent stem cell-derived cultures for neurodegenerative disease modelling.", Molecular Neurodegeneration, May 22, 2018, vol. 13, No. 27, pp. 1-15.
Office Action for corresponding SG Application No. 11202113100T, dated Jul. 13, 2023, 14 pages.
European Search Report for corresponding European Application No. 20812823.1, mailed May 8, 2023, 15 pages.
International Search Report for corresponding PCT/JP2020/021177, mailed Aug. 18, 2020, 5 pages.
Office Action for corresponding SG Application No. 11202113016U, dated Jul. 13, 2023, 11 pages.
Supplementary European Search Report received in corresponding Application No. EP20814392, dated May 26, 2023, 12 pages.
Tong et al., "Five-class differential diagnostics of neurodegenerative diseases using random undersampling boosting", NeuroImage: Clinical, 15, Mar. 9, 2017 pp. 613-624.
[Corrected] Supplementary European Search Report received in corresponding Application No. EP20814392, dated May 5, 2023, 12 pages.
[Corrected] Supplementary European Search Report received in corresponding Application No. EP 20814392.5, dated Jun. 5, 2023, 12 pages.

* cited by examiner

INFORMATION PROCESSING DEVICE, SCREENING DEVICE, INFORMATION PROCESSING METHOD, SCREENING METHOD, AND PROGRAM

TECHNICAL FIELD

The present invention relates to an information processing device, a screening device, an information processing method, a screening method, and a program.

The present application is a national phase entry of International Patent Application No. PCT/JP2020/021384 filed on May 29, 2020, which is based upon and claims the right of priority to Japanese Patent Application No. 2019-103294, filed May 31, 2019, the content of which is incorporated herein by reference.

BACKGROUND ART

Technology that uses machine learning to determine microscopic images of cells and tissues is being studied. For example, Non-Patent Document 1 states that it was possible to identify the nuclei, life and death of cells, and cell types (whether or not the cells were nerve cells) by a trained machine learning model of microscopic images of cultured cells. Non-Patent Document 2 describes that it was possible to identify lung adenocarcinoma, squamous cell carcinoma, and healthy lung tissues by a trained machine learning model of microscopic images of pathologic tissues of lung cancer.

CITATION LIST

Patent Literature

Non-Patent Literature

[Non-Patent Document 1]
Christiansen E. M., et al., In Silico Labeling: Predicting Fluorescent Labels in Unlabeled Images, Cell, 173 (3), 792-803, 2018.
[Non-Patent Document 2]
Coudray N. et al., Classification and mutation prediction from non-small cell lung cancer histopathology images using deep learning, Nat Med., 24 (10), 1559-1567, 2018.

SUMMARY OF INVENTION

Technical Problem

Intractable neurological diseases such as amyotrophic lateral sclerosis (ALS) require early diagnosis and early treatment. Therefore, it is required to diagnose a presymptomatic status before a subject is diagnosed as having an intractable neurological disease using conventional diagnostic methods. The term "presymptomatic status" refers to a state where mild symptoms appear, although the symptoms have not yet developed.

However, the trained models described in Non-Patent Document 1 and 2 determine the current state of cells and tissues, but do not predict whether or not the subject is in a presymptomatic status of an intractable neurological disease. In other words, the trained models described in Non-Patent Documents 1 and 2 do not predict that a subject will develop an intractable neurological disease at some point in the future, although the subject does not have an intractable neurological disease at the current time.

An object of the present invention is to provide an information processing device, a screening device, an information processing method, a screening method, and a program capable of accurately predicting that a subject will develop an intractable neurological disease based on images of cells differentiated from pluripotent stem cells derived from the subject.

Solution to Problem

According to an aspect of the present invention, there is provided an information processing device including: an acquirer configured to acquire images obtained by imaging cells differentiated from pluripotent stem cells derived from a subject; and a predictor configured to input the images acquired by the acquirer to a model trained on data in which information indicating at least an intractable neurological disease is associated with an image obtained by imaging cells of the intractable neurological disease differentiated from pluripotent stem cells, and predict an onset of the intractable neurological disease of the subject based on output results of the model to which the images were input.

Advantageous Effects of Invention

According to an aspect of the present invention, it is possible to accurately predict that a subject will develop an intractable neurological disease based on images of cells differentiated from pluripotent stem cells derived from the subject.

DESCRIPTION OF EMBODIMENTS

Hereinafter, an information processing device, a screening device, an information processing method, a screening method, and a program according to the present embodiment will be described with reference to the drawings.

First Embodiment

[Overall Configuration]

Figure 1:
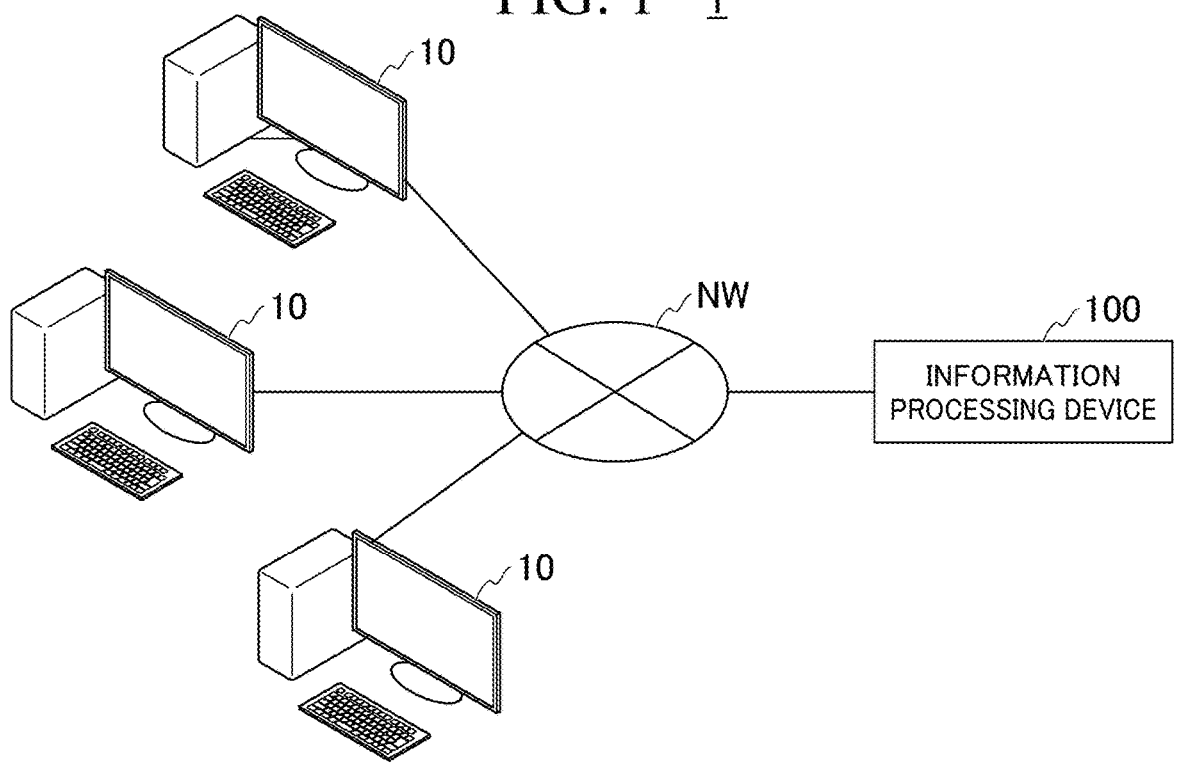
FIG. 1 is a view illustrating an example of an information processing system including an information processing device according to a first embodiment.

FIG. 1 is a view illustrating an example of an information processing system 1 including an information processing device 100 according to a first embodiment. The information processing system 1 according to the first embodiment includes, for example, one or more terminal devices 10 and the information processing device 100. These devices are connected to each other via a network NW. The network NW includes, for example, the Internet, a wide area network (WAN), a local area network (LAN), a provider terminal, a wireless communication network, a wireless base station, a dedicated line, and the like. All of the devices illustrated in FIG. 1 in a combination need not be able to communicate with each other, and the network NW may include some local networks.

The terminal device 10 is, for example, a terminal device including an input device, a display device, a communication device, a storage device, and a computing device. Specifically, the terminal device 10 can be a personal computer, a cell phone, or a tablet terminal. The communication device includes a network card such as a network interface card (NIC), a wireless communication module, and the like. For example, the terminal device 10 may be installed in a facility (for example, a research institute, a university, or a company) that conducts research and development of new drugs using pluripotent stem cells.

The pluripotent stem cells mentioned above include, for example, embryonic stem cells (ES cells), induced pluripotent stem cells (iPS cells), embryonic stem (ntES) cells derived from cloned embryos obtained by nuclear transplantation, sperm stem cells ("GS cells"), embryonic germ cells ("EG cells"), induced pluripotent stem cells (iPS cells), and the like. Preferred pluripotent stem cells are ES cells, iPS cells, and ntES cells. More preferred pluripotent stem cells are human pluripotent stem cells, particularly human ES cells and human iPS cells. Furthermore, the cells that can be used in the present invention are not only pluripotent stem cells, but also a group of cells induced by so-called "direct reprogramming", in which the cells are directly induced to differentiate into desired cells without going through pluripotent stem cells.

For example, an employee or the like working at a facility may capture an image of a desired cell induced to differentiate from pluripotent stein cells using a microscope or the like, and transmit the captured digital image (hereinafter, referred to as a cell image IMG) to the information processing device 100 via the terminal device 10.

When the information processing device 100 receives the cell image IMG from the terminal device 10, by using deep learning, based on the cell image IMG, it is predicted that the subject from whom the pluripotent stem cells were extracted before differentiation induction will develop an intractable neurological disease such as ALS at some point in the future.

The cells induced to differentiate from pluripotent stem cells may be, for example, cells related to the intractable neurological disease such as ALS, and specifically, may be, for example, nerve cells, glial cells, vascular endothelial cells, pericytes, choroid plexus cells, immune system cells, and the like. Examples of the neurodegenerative diseases include Alzheimer's disease, Parkinson's disease, amyotrophic lateral sclerosis (ALS), spinocerebellar degeneration, frontotemporal lobar degeneration, Lewy body dementia, multiple system atrophy, Huntington's disease, progressive supranuclear palsy, or corticobasal degeneration. The cells induced to differentiate from pluripotent stem cells may be imaged alive or may be imaged after being fixed and immunochemically stained.

The cells of intractable neurological diseases differentiated from pluripotent stem cells are referred to as cells differentiated from pluripotent stem cells and cells that show a phenotype of an intractable neurological disease. As the cells of intractable neurological diseases differentiated from pluripotent stem cells, for example, cells differentiated from pluripotent stem cells derived from patients with intractable neurological diseases such as ALS, or cells differentiated from pluripotent stem cells derived from healthy subjects in which genetic mutations that cause the onset of intractable neurological diseases such as ALS are introduced, can be used.

For example, in a case where the cells induced to differentiate from pluripotent stem cells are nerve cells such as motor nerve cells, the information processing device 100 predicts that the subject from whom the pluripotent stem cells were extracted will develop ALS which is one of the intractable neurological diseases at some point in the future. ALS is a disease in which the motor nervous system is damaged by the gradual death or loss of function of nerve cells.

Therefore, by predicting that the nerve cells induced to differentiate from pluripotent stem cells will show a phenotype of the intractable neurological disease such as ALS at some point in the future, the information processing device 100 determines whether or not the subject will develop the intractable neurological diseases such as ALS at some point in the future. A phenotype is a genotype of an organism expressed as a trait, and includes, for example, the morphology, structure, behavior, and physiological properties of the organism. Examples of the phenotype of the intractable neurological disease include cell morphology. In the following, as an example, a case is described where the cells induced to differentiate from pluripotent stem cells are nerve cells.

[Configuration of Information Processing Device]

Figure 2:
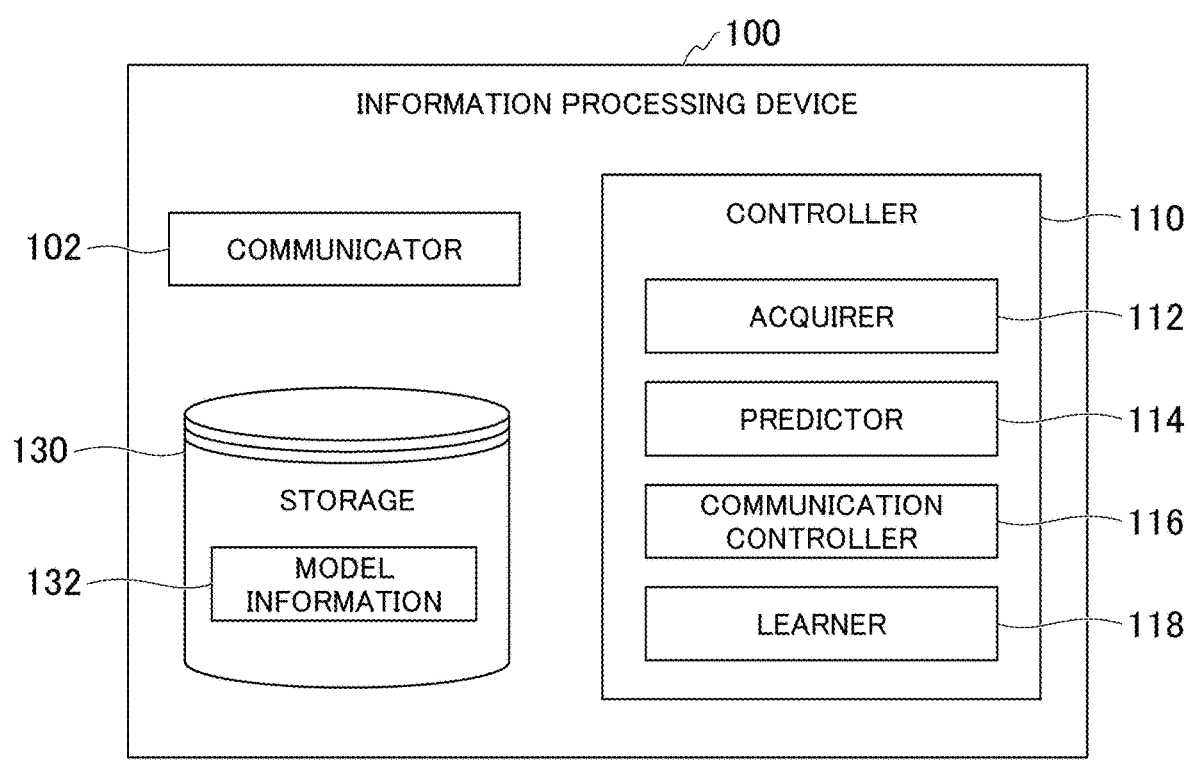
FIG. 2 is a view illustrating an example of a configuration of the information processing device according to the first embodiment.

FIG. 2 is a view illustrating an example of a configuration of the information processing device 100 according to the first embodiment. As illustrated in the drawing, the information processing device 100 includes, for example, a communicator 102, a controller 110, and a storage 130.

The communicator 102 includes a communication interface, such as an NIC. The communicator 102 communicates with the terminal device 10 and the like via the network NW.

The controller 110 includes, for example, an acquirer 112, a predictor 114, a communication controller 116, and a learner 118.

The components of the controller 110 are realized, for example, by a processor such as a central processing unit (CPU) or a graphics processing unit (GPU) executing a program stored in the storage 130. Some or all of the components of the controller 110 may be realized by hardware (circuitry) such as a large-scale integration (LSI), an application specific integrated circuit (ASIC), or a field-programmable gate array (FPGA), or may be realized by the cooperation of software and hardware.

The storage 130 is realized, for example, by a storage device such as a hard disk drive (HDD), a flash memory, an electrically erasable programmable read only memory (EEPROM), a read only memory (ROM), a random access memory (RAM), and the like. In addition to various programs such as firmware and application programs, model information 132 is stored in the storage 130. The model information 132 will be described later.

[Runtime Processing Flow]

Figure 3:
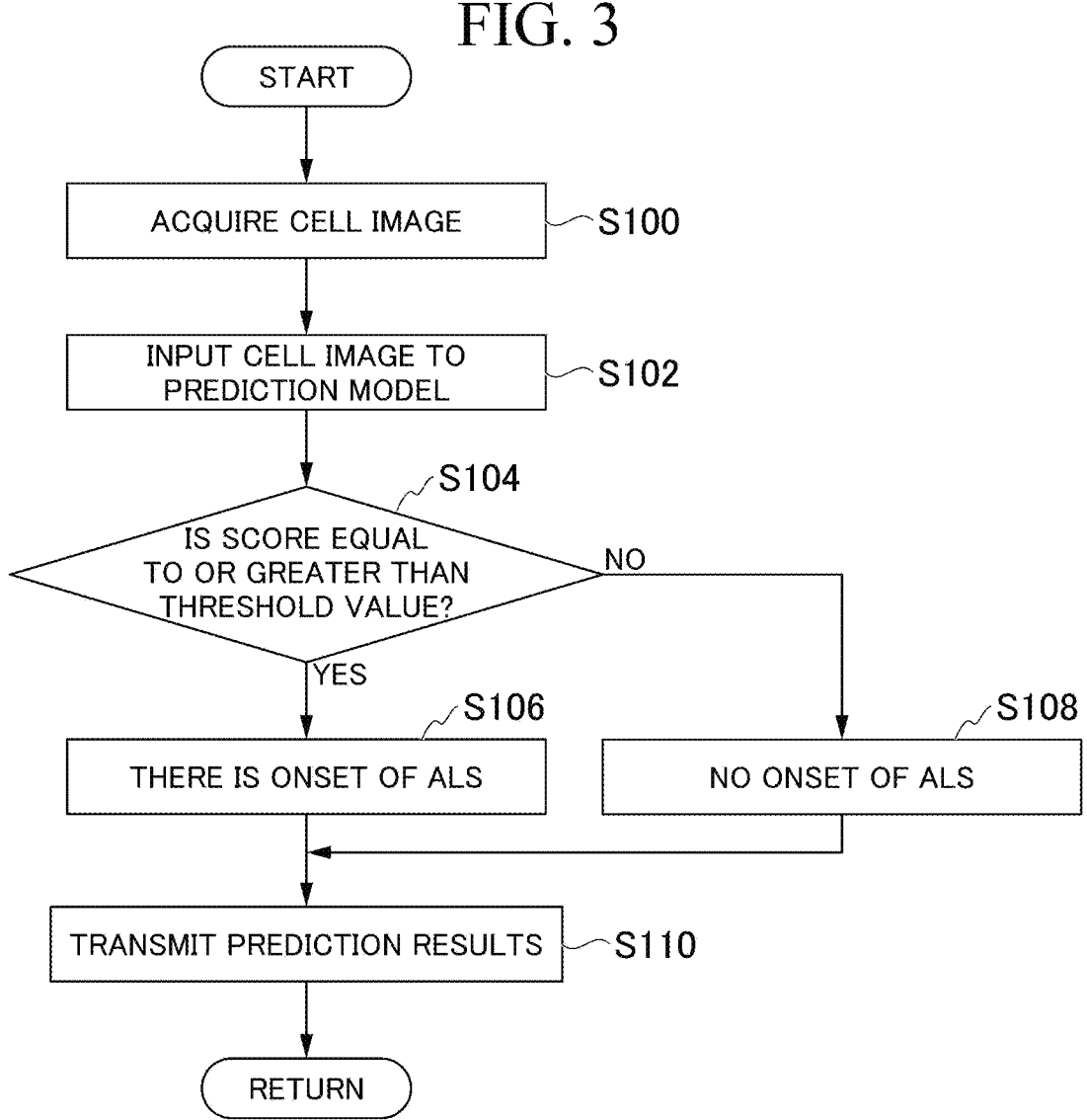
FIG. 3 is a flowchart illustrating a flow of a sequence of runtime processing by a controller according to the first embodiment.

Hereinafter, a flow of a series of runtime processing by the controller 110 according to the first embodiment will be described with reference to a flowchart. Runtime is a state where a prediction model MDL that has already been trained is used. FIG. 3 is a flowchart illustrating a flow of a series of runtime processing by the controller 110 according to the first embodiment. The process in the present flowchart may be repeated in a predetermined cycle, for example.

First, the acquirer 112 acquires the cell image IMG of a nerve cell from the terminal device 10 via the communicator 102 (step S100). The nerve cells to be imaged may be fixed and immunostained. Specifically, the nerve cells to be imaged may be, for example, nerve cells that have been immunostained with an anti-neurofilament H antibody or the like after being fixed with reagents such as formaldehyde or paraformaldehyde.

Next, the predictor 114 inputs the cell image IMG acquired by the acquirer 112 to the prediction model MDL indicated by the model information 132 (step S102).

The model information 132 is information (program or data structure) that defines the prediction model MDL for predicting that a nerve cell will exhibit the phenotype of the intractable neurological disease such as ALS, based on the cell image IMG of the nerve cells. The prediction model MDL is implemented, for example, by one or a plurality of neural networks. The neural network can be, for example, a convolutional neural network (CNN).

The model information 132 includes, for example, various types of information such as coupling information on how the units included in each of an input layer, one or more hidden layers (intermediate layers), and an output layer that configure each neural network are coupled with each other, coupling coefficients given to the data input and output between the coupled units, and the like. The coupling information includes, for example, the number of units included in each layer, information specifying the type of the units to which each unit is coupled, the activation function that realizes each unit, and the gates provided between the units in the hidden layer. The activation function that realizes the units may be, for example, a normalized linear function (ReLU function), a sigmoid function, a step function, or any other function. The gates, for example, selectively pass or weight the data transmitted between the units depending on the value (for example, 1 or 0) returned by the activation function. The coupling coefficients include, for example, the weight given to the output data when the data is output from a unit in one layer to a unit in a deeper layer, in the hidden layer of the neural network. The coupling coefficients may include the inherent bias component of each layer, and the like.

Figure 4:
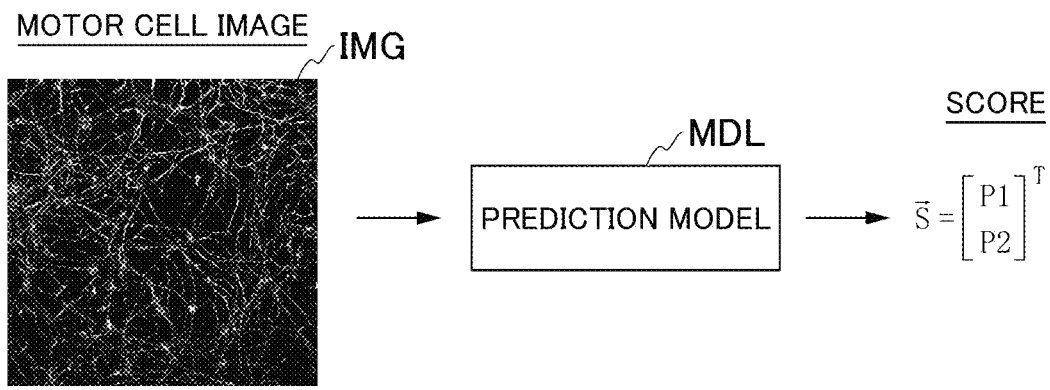
FIG. 4 is a view illustrating an example of a prediction model according to the first embodiment.

FIG. 4 is a view illustrating an example of the prediction model MDL according to the first embodiment. As illustrated in the drawing, the prediction model MDL is a single neural network that has learned to output a score indicating the likelihood that the nerve cell will show a phenotype of the intractable neurological disease as a likelihood or a probability, when the cell image IMG of the nerve cell is input. The neural network includes the CNN. Specifically, the prediction model MDL is a neural network that includes a plurality (for example, thirteen or sixteen layers) of convolutional layers and a plurality (for example, three layers) of fully-connected layers. The score may be represented by a two-dimensional vector of which elements are respectively a probability P1 indicating the phenotype of the intractable neurological disease, for example, indicating the nerve cell death and the onset of the intractable neurological disease, and a probability P2 indicating that the phenotype of intractable neurological disease is not shown, for example, indicating that nerve cells do not die and do not develop the intractable neurological disease.

Description will return to the flowchart in FIG. 3. Next, the predictor 114 determines whether or not the probability P1 which is included as an element in the score output by the prediction model MDL is equal to or greater than a threshold value (step S104).

In a case where the probability P1 is equal to or greater than the threshold value, the predictor 114 predicts the onset of the intractable neurological disease since the nerve cells have a high probability of showing the phenotype of the intractable neurological disease (step S106), and in a case where the probability P1 is less than the threshold value, the predictor 114 predicts that the intractable neurological disease will not develop since nerve cells have a low probability of showing the phenotype of the intractable neurological disease (step S108).

Next, the communication controller 116 transmits the prediction results by the predictor 114 to the terminal device 10 via the communicator 102 (step S110). For example, the communication controller 116 may transmit the information indicating whether or not the nerve cells show the phenotype of the intractable neurological disease, or may transmit the information indicating the presence or absence of the onset of the intractable neurological disease.

For example, in a case where the information indicating that the nerve cells show the phenotype of the intractable neurological disease is transmitted to the terminal device 10, the user operating the terminal device 10 can ascertain whether the nerve cells shown in the cell image IMG transmitted to the information processing device 100 are destined to show the phenotype of the intractable neurological diseases such as ALS at some point in the future, or are destined not to show the phenotype of the intractable neurological diseases such as ALS. In other words, the user can know whether or not the subject from whom the pluripotent stem cells before differentiation induction into the nerve cells were extracted will develop the intractable neurological disease such as ALS in the future.

[Training Processing Flow]

Hereinafter, a flow of a series of training processing by the controller 110 according to the first embodiment will be described with reference to a flowchart. Training is a state where the prediction model MDL used in runtime is trained.

Figure 5:
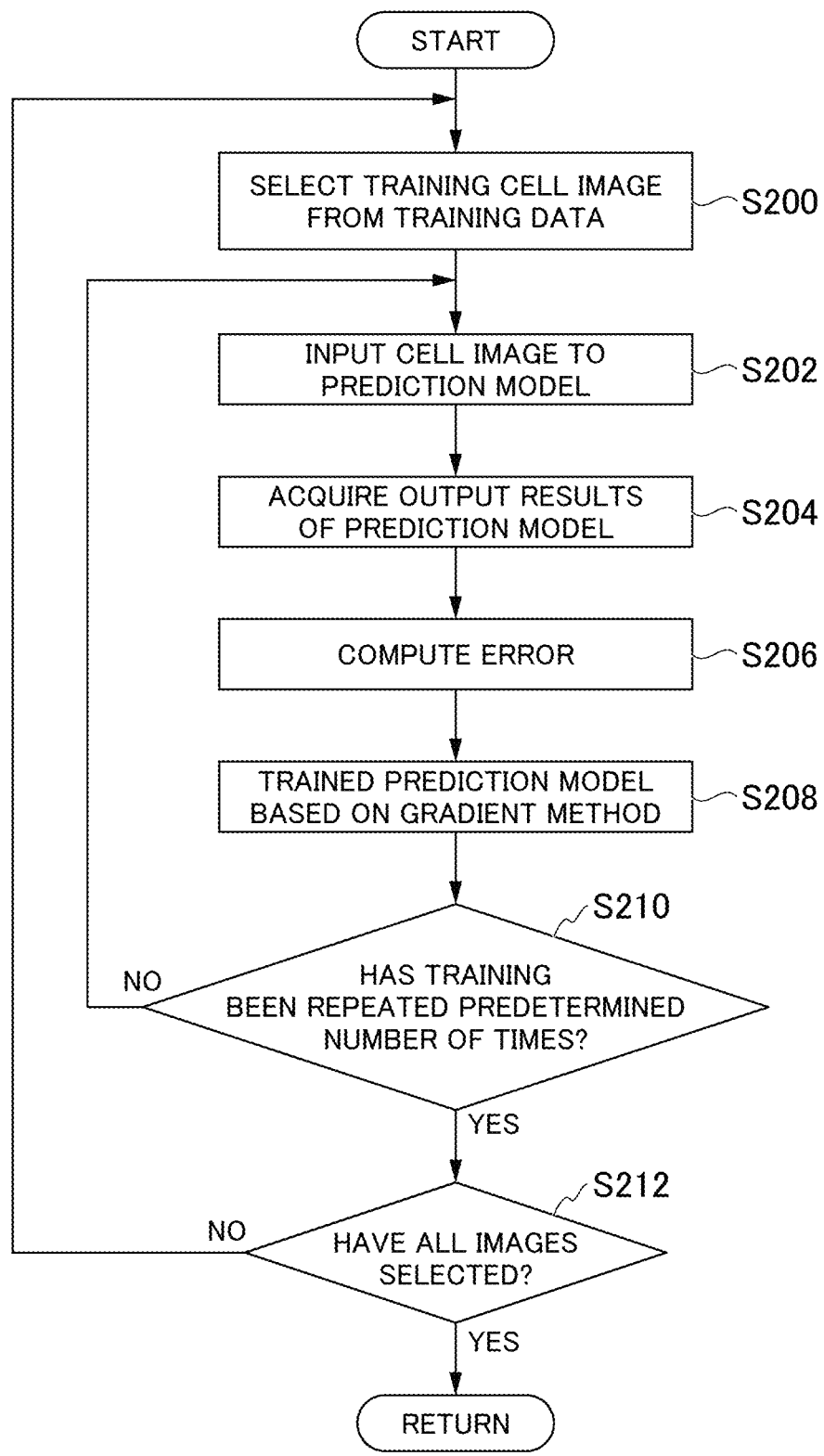
FIG. 5 is a flowchart illustrating a series of training processing by a controller according to the first embodiment.

FIG. 5 is a flowchart illustrating a series of training processing by the controller 110 according to the first embodiment.

First, the learner 118 selects one cell image IMG from among the plurality of cell images IMG included in the training data in order to train the prediction model MDL (step S200). For example, the training data is data in which information indicating that the nerve cells show the phenotype of the intractable neurological disease such as ALS at some point in the future is associated with the cell image IMG obtained by imaging the nerve cells induced to differentiate from pluripotent stem cells, as a teaching label (also referred to as a target). In other words, the training data is a dataset that combines input data and output data, while the cell image IMG obtained by imaging the nerve cells induced to differentiate from pluripotent stem cells is input data, and the information indicating the phenotype of the intractable neurological disease is correct output data. The phenotype of the intractable neurological disease at some point in the future represents a more prominent phenotype of the neurodegenerative disease than that at the time when the cell image IMG was captured.

For example, the pluripotent stem cells of the patient with the intractable neurological disease are induced to differentiate to prepare a plurality of nerve cells, and each of the plurality of prepared nerve cells is imaged to generate the plurality of cell images IMG. Meanwhile, the pluripotent stem cells of the healthy subject are induced to differentiate to prepare a plurality of nerve cells, and each of the plurality of prepared nerve cells is imaged to generate the plurality of cell images IMG.

Information (for example, score S=[1.0, 0.0]) indicating the phenotype of the intractable neurological disease is associated with the cell images IMG obtained by imaging the nerve cells derived from the patients with the intractable neurological disease as a teaching label, and information (for example, score S=[0.0, 1.0]) indicating that the phenotype of the intractable neurological disease is not shown is associated with the cell images IMG obtained by imaging the nerve cells derived from the healthy subject as a teaching label. In this manner, the plurality of cell images IMG with which the teaching labels are associated are prepared as training data.

Next, the learner 118 inputs the selected cell image IMG to the prediction model MDL (step S202).

Next, the learner 118 acquires the score, which is the output result of the prediction model MDL to which the cell image IMG is input (step S204).

Next, the learner 118 computes the error (also referred to as loss) between the score output by the prediction model MDL and the score associated with the cell image IMG input to the prediction model MDL as a teaching label (step S206).

Next, the learner 118 determines the parameters of the prediction model MDL such that the error is reduced based on a gradient method such as error inverse propagation (step S208).

Next, the learner 118 determines whether or not the training of the prediction model MDL has been repeated a predetermined number of times E (for example, approximately 30 times) (step S210), and in a case where the predetermined number of times E has not been reached, the processing returns to S202, and the same cell image IMG used for training in the previous processing is input to the prediction model MDL to repeatedly train the prediction model MDL.

Next, the learner 118 selects all the cell images IMG included in the training data and determines whether or not the prediction model MDL has been trained (step S212), and in a case where not all the cell images IMGs have been selected yet, the process returns to S200, and the cell images IMG different from the previously selected cell images IMG are reselected to repeatedly train the prediction model MDL for a predetermined number of times E. Meanwhile, in a case where the learner 118 selects all the cell images IMG, the process of this flowchart is ended.

According to the above-described first embodiment, the information processing device 100 trains the prediction model MDL based on the training data in which the information indicating at least the intractable neurological disease such as ALS is associated with the image obtained by imaging the cells of the intractable neurological disease such as ALS induced to differentiate from pluripotent stem cells, as the teaching label. Then, the information processing device 100 acquires the cell images IMG obtained by imaging the cells differentiated from the pluripotent stem cells derived from the subject, and inputs the acquired images to the prediction model MDL that has been trained, and predicts the onset of the intractable neurological disease such as ALS of the subject based on the output results of the prediction model MDL. Therefore, it is possible to accurately predict that the subject will develop an intractable neurological disease such as ALS in the future.

In general, even in a case of cell images of cells in which a phenotype (for example, cell death) of an intractable neurological disease will appear at some point in the future, it is difficult to observe changes in phenotype in cell images in the early stages when the intractable neurological disease has not yet developed. On the other hand, in the present embodiment, since a prediction model MDL implemented by the CNN or the like is used, it is possible to expect that features such as minute changes in the cell structure and relative positional relationships between cells, which are difficult to observe with the naked eye in the cell images, can be calculated as convolutional feature amounts in the hidden layer. Accordingly, intractable neurological diseases that cannot be caught by humans visually checking cell images can be discovered at an early stage. In other words, it can be predicted that patients with a presymptomatic status who have not been diagnosed as having an intractable neurological disease by conventional diagnostic methods will develop the intractable neurological disease. As a result, treatment can be started at an early stage.

Modification Example of First Embodiment

Hereinafter, a modification example of the first embodiment will be described. In the above-described first embodiment, the prediction model MDL is described as a single neural network, but is not limited thereto. For example, the prediction model MDL may be a model that combines the plurality of neural networks.

Figure 6:
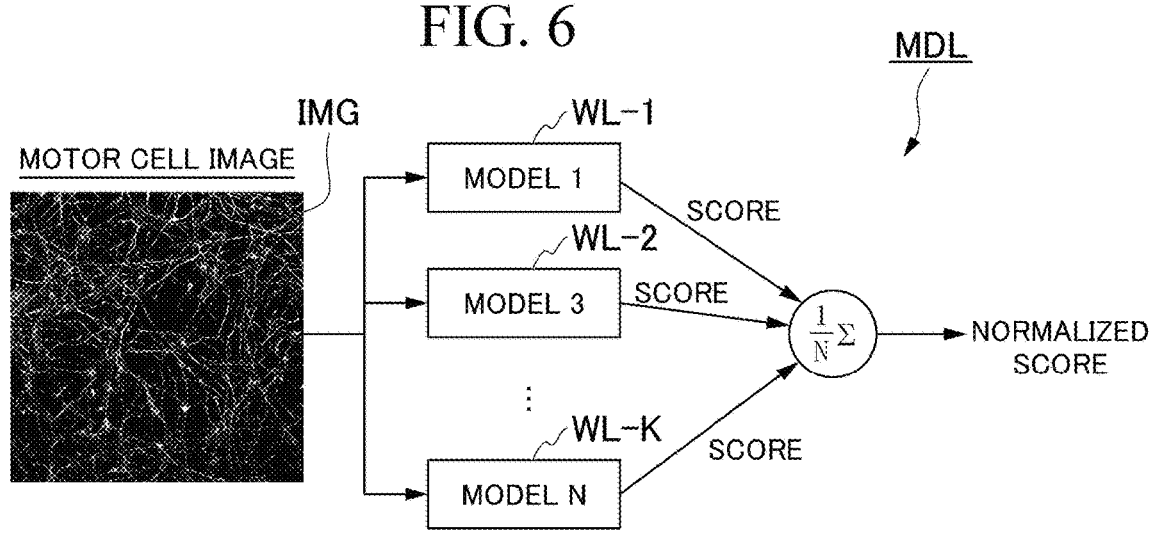
FIG. 6 is a view illustrating another example of the prediction model according to the first embodiment.

FIG. 6 is a view illustrating another example of the prediction model MDL according to the first embodiment. As illustrated in the drawing, the prediction model MDL includes, for example, K models WL-1 to WL-K. Each of the models WL is a weak learner that has learned to output a score indicating the likelihood that the nerve cell will show a phenotype of the intractable neurological disease when the cell image IMG of the nerve cell is input. For example, the model WL includes the CNN. Each model WL is in a parallel relationship with each other. The method of combining multiple weak learners to generate a single learning model in this manner is called ensemble learning.

For example, the prediction model MDL normalizes the scores of each model WL, which is a weak learner, and outputs the normalized score. The normalization of the score is shown in Equation (1). Equation (1) is implemented, for example, by a fully-connected layer.

[Math. 1]

$$S = \frac{1}{N}\sum_{i=1}^{N} s_i \qquad (1)$$

S in the equation represents the normalized score, and $s_i$ represents the score of the i-th model WL. The scores $s_i$ and S are two-dimensional vectors (=[P1, P2]) of which elements are, for example, respectively, the probability P1 indicating the phenotype of the intractable neurological disease, for example, indicating cell death, and the probability P2 indicating that the phenotype of the intractable neurological disease is not shown, for example, indicating that the nerve cells will not die. As shown in Equation (1), the prediction model MDL may normalize the scores by dividing the sum of the scores of all models WL by K which is the total number of models WL. By using ensemble learning in this manner, we can improve the prediction accuracy of cell death for unknown (unlabeled) data that was not used in the training.

In the above-described first embodiment, the training data is described as data in which a score indicating whether or not the nerve cells show the phenotype of the intractable neurological disease at some point in the future is associated with the cell image IMG, as the teaching label, but the present invention is not limited thereto. For example, the training data may be data in which, in addition to the above-described score, the age at the onset of the intractable neurological disease, the symptomatic period of the intractable neurological disease, or the like is further associated with the cell image IMG. The symptomatic period is, for example, a period from the onset of the intractable neurological disease until the symptoms reach a predetermined state (for example, a state that requires a respirator).

For example, in a case where the prediction model MDL is trained using the training data in which the age of the onset of the intractable neurological disease is associated with the cell image IMG, the prediction model MDL outputs the age of the onset of the intractable neurological disease in addition to the score when the cell image IMG is input. In this case, the predictor 114 predicts the time (period) until the subject develops the intractable neurological disease, based on the age output by the prediction model MDL.

For example, in a case where the prediction model MDL is trained using the training data in which the symptomatic period of the intractable neurological disease is associated with the cell image IMG, the prediction model MDL outputs the symptomatic period of the intractable neurological disease in addition to the score when the cell image IMG is input. The predictor 114 predicts the progression rate of the symptoms of the intractable neurological disease in a case where the subject develops the intractable neurological disease, based on the symptomatic period output by the prediction model MDL.

In ALS, which is one of the intractable neurological diseases, there are two types: inherited and sporadic. Therefore, the training data may be data in which a three-dimensional score (=[P1(H), P1(S), P2]), of which elements are a probability P1(H) indicating the likelihood of having inherited ALS, a probability P1(S) indicating the likelihood of having sporadic ALS, and a probability P2 indicating the likelihood of not having any ALS, is associated with the cell image IMG as a teaching label.

For example, a score S=[1.0, 0.0, 0.0]) may be associated with the cell image IMG of the nerve cells prepared by differentiation induction of the pluripotent stem cells from the patient with inherited ALS as a teaching label, and a score S=[1.0, 0.0, 0.0]) may be associated with the cell image IMG of the nerve cells prepared by differentiation induction of the pluripotent stem cells from the patient with sporadic ALS as a teaching label.

By training the prediction model MDL using such training data, it is possible not only to predict whether or not the intractable neurological disease such as ALS will develop, but also to predict what type of intractable neurological disease will develop.

The training data may further be data in which, in addition to the cell image IMG, the teaching label is associated with personal information indicating the sex or the presence or absence of genetic polymorphisms or specific genes (for example, SOD1 gene) of the patient with the intractable neurological disease. Personal information may further include a variety of information, such as age, weight, height, lifestyle, presence or absence of disease, and family medical history.

In a case of using the prediction model MDL that has been trained using the cell image IMG and the personal information with which such a teaching label is associated, the acquirer 112 acquires the cell images IMG of the nerve cells and also acquires the personal information indicating the sex of the subject, the presence or absence of genetic polymorphism or a specific gene. In addition, the predictor 114 inputs the cell image IMG and the personal information to the prediction model MDL that has been trained, and predicts that the subject will develop the intractable neurological disease such as ALS based on the output results of the prediction model MDL.

Until now, the intractable neurological disease such as sporadic ALS described above have been considered to be developed without genetic influence. However, it is known that, in a case where one of identical twins develops sporadic ALS, the other will also develop sporadic ALS, and this means that even sporadic ALS has some genetic factors. Therefore, by inputting the genetic polymorphism to the prediction model MDL, it is possible to expect that the prediction model MDL learns some causal relation between the onset of sporadic ALS and genetic factors.

In addition to the CNN, the prediction model MDL may include, for example, a recurrent neural network (RNN) of which the intermediate layer is a long short-term memory (LSTM).

Second Embodiment

Hereinafter, a second embodiment will be described. The second embodiment describes a screening device 100A that inputs the cell images IMG of the cells which are differentiated from the pluripotent stem cells derived from the patient with the intractable neurological disease such as ALS and are in contact with the test substance to the prediction model MDL, and determines whether or not the test substance is a preventive or a therapeutic agent for the intractable neurological diseases based on the output results of the prediction model MDL. Hereinafter, the following description focuses on the differences from the first embodiment, and the points in common with the first embodiment will be omitted. In the description of the second embodiment, the same reference numerals will be given to the same parts as those of the first embodiment.

Figure 7:
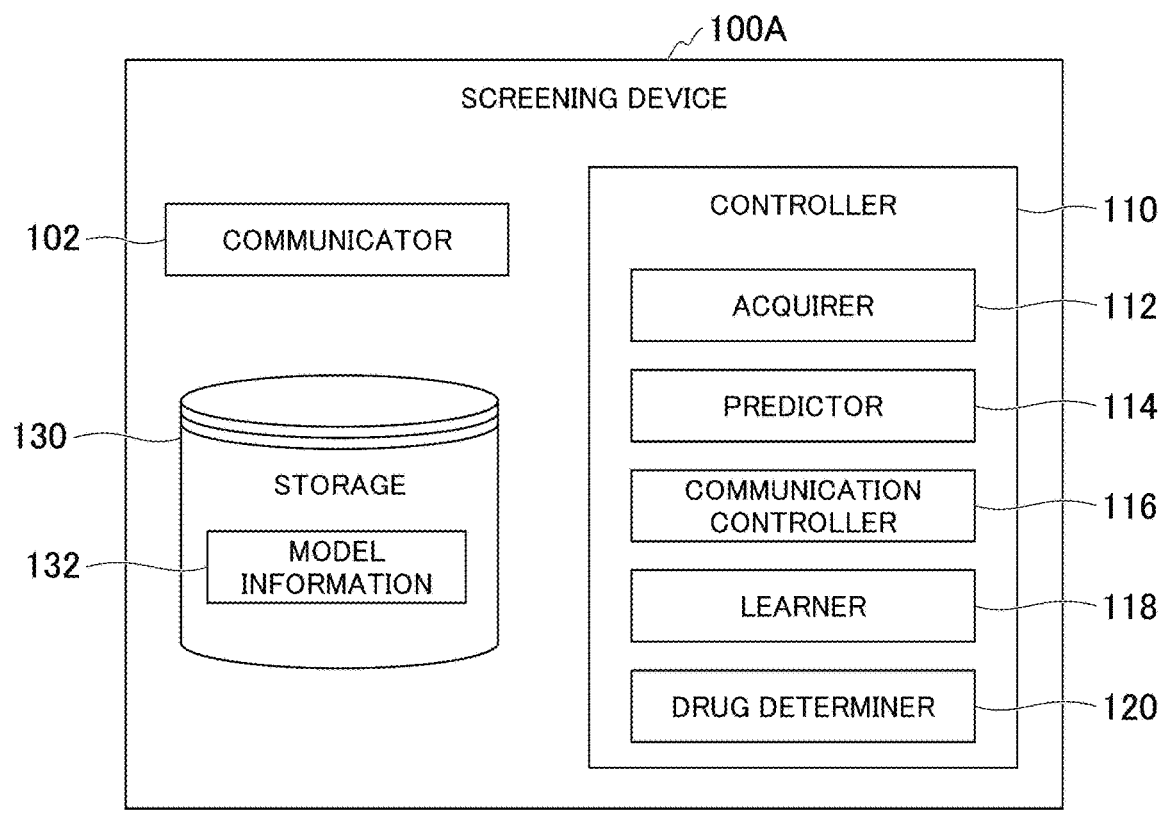
FIG. 7 is a view illustrating an example of a configuration of a screening device according to a second embodiment.

FIG. 7 is a view illustrating an example of a configuration of the screening device 100A according to the second embodiment. As illustrated in the drawing, the screening device 100A includes the configuration of the information processing device 100 according to the above-described first embodiment. Specifically, the screening device 100A includes the communicator 102, a controller 110A, and the storage 130.

The controller 110A according to the second embodiment further includes a drug determiner 120 in addition to the above-described acquirer 112, predictor 114, communication controller 116, and learner 118.

The acquirer 112 according to the second embodiment acquires the images obtained by imaging the cells of the intractable neurological disease, which are in contact with the test substance and differentiated from the pluripotent stem cells derived from the patient with the intractable neurological disease such as ALS. The test substance is not particularly limited, and examples thereof include natural compound libraries, synthetic compound libraries, existing drug libraries, metabolite libraries, and the like. In the present embodiment, a preventive for the intractable neurological disease is a drug that can suppress the onset of the intractable neurological disease or reduce the symptoms when administered to a target before the onset of the intractable neurological disease. A therapeutic agent for the intractable neurological disease is a drug that can reduce the symptoms of the intractable neurological disease when administered to a patient after the onset of the intractable neurological disease.

The learner 118 according to the second embodiment trains the prediction model MDL based on the training data in the same manner as that of the above-described first embodiment.

The predictor 114 according to the second embodiment inputs the images acquired by the acquirer 112 to the prediction model MDL that has been trained. In addition, the predictor 114 predicts whether or not the phenotype (for example, cell death) of the intractable neurological disease such as ALS will appear in the cells to which the test substance was administered, based on the output results of the prediction model MDL with the image input.

The drug determiner 120 determines whether the test substance is a preventive or a therapeutic agent for the neurodegenerative disease based on the prediction results of the predictor 114.

For example, the drug determiner 120 may determine that the test substance is a preventive or a therapeutic agent for the intractable neurological disease such as ALS in a case where the following condition (1) is satisfied, and may determine that the test substance is neither a preventive nor a therapeutic agent for the intractable neurological disease such as ALS in a case where the condition (2) is satisfied.

Condition (1): The score output by the prediction model MDL to which the image is input is equal to or less than a threshold value, and it is predicted that the phenotype of the intractable neurological disease such as ALS will not appear in the cells to which the test substance is administered.

Condition (2): The score output by the prediction model MDL to which the image is input is equal to or greater than a threshold value, and it is predicted that the phenotype of the intractable neurological disease such as ALS will appear in the cells to which the test substance is administered.

According to the above-described second embodiment, the screening device 100A acquires images obtained by imaging cells of intractable neurological disease such as ALS, which are in contact with the test substance and differentiated from pluripotent stem cells, inputs the acquired images to the prediction model MDL that has been trained, and predicts whether or not the phenotype of the intractable neurological disease such as ALS will appear in the cells of the intractable neurological disease such as ALS which are in contact with the test substance, based on output results of the prediction model MDL to which the images were input, and determines whether the test substance is a preventive or a therapeutic agent for the intractable neurological disease such as ALS based on prediction results of whether or not the phenotype will appear in the cells. As a result, based on the images of the cells differentiated from the pluripotent stem cells, it is possible to efficiently discover new drugs that can be a preventive or a therapeutic agent for the intractable neurological disease such as ALS.

<Hardware Configuration>

Figure 8:
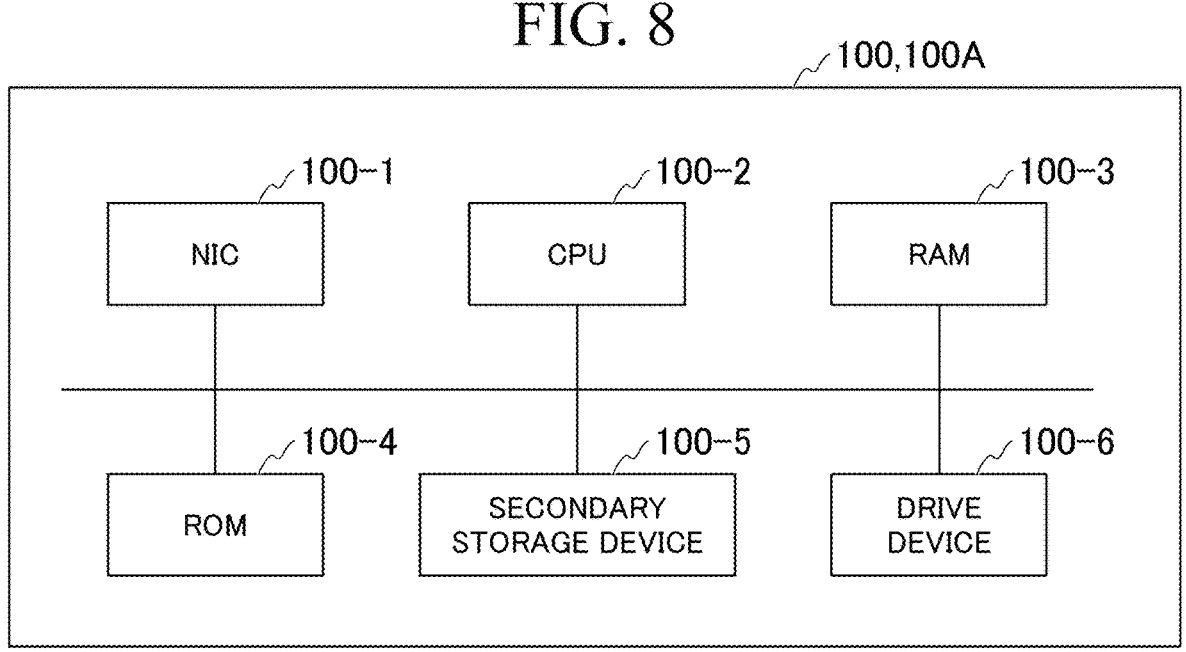
FIG. 8 is a view illustrating an example of a hardware configuration of the information processing device and the screening device of the embodiments.

The information processing device 100 and the screening device 100A of the above-described embodiment are realized, for example, by a hardware configuration as illustrated in FIG. 8. FIG. 8 is a view illustrating an example of the hardware configuration of the information processing device 100 and the screening device 100A of the embodiments.

The information processing device 100 has a configuration in which a NIC 100-1, a CPU 100-2, a RAM 100-3, a ROM 100-4, a secondary storage device 100-5 such as a flash memory or an HDD, and a drive device 100-6 are connected to each other by an internal bus or a dedicated communication line. A portable storage medium, such as an optical disk, is attached to the drive device 100-6. A program stored in a portable storage medium attached to the secondary storage device 100-5 or the drive device 100-6 is expanded into the RAM 100-3 by a DMA controller (not illustrated) or the like, and executed by the CPU 100-2 to realize the controllers 110 and 110A. The program that the controller 110 or 110A refers to may be downloaded from another device via the network NW.

Expression Example 1

The above-described embodiments can be expressed as follows.

An information processing device including: a processor; and a memory for storing a program, the device configured to, by executing the program by the processor, acquire images obtained by imaging cells differentiated from pluripotent stem cells derived from a subject, and input the acquired images to a model trained on data in which information indicating at least an intractable neurological disease is associated with the image obtained by imaging the cells of the intractable neurological disease differentiated from the pluripotent stem cells, and predict an onset of the intractable neurological disease of the subject based on output results of the model to which the images were input.

Expression Example 2

The above-described embodiments can also be expressed as follows.

A screening device including: a processor; and a memory for storing the program, the device configured to, by executing the program by the processor, acquire images obtained by imaging cells of an intractable neurological disease, which are in contact with a test substance and differentiated from pluripotent stem cells, inputs the acquired images to a model trained on data in which information indicating at least a phenotype of the intractable neurological disease is associated with the image obtained by imaging the cells of the intractable neurological disease differentiated from the pluripotent stem cells, and predict whether or not the phenotype of the intractable neurological disease will appear in the cells of the intractable neurological disease which are in contact with the test substance, based on the output results of the model to which the images were input, and determine whether the test substance is a preventive or a therapeutic agent for the neurodegenerative disease based on prediction results.

Above, although the aspects for carrying out the present invention have been described using the embodiments, the present invention is not limited to the above-described embodiments, and various modifications and substitutions can be made without departing from the gist of the present invention.

EXAMPLE

Experiment Example 1

(Training Data Preparation)
Spinal motoneurons were prepared using iPS cells prepared from sixteen healthy subjects and iPS cells prepared from sixteen ALS patients with SOD1 mutations. The cell images of the prepared motoneurons were acquired using InCell 6000 (GE healthcare).

Figure 9:
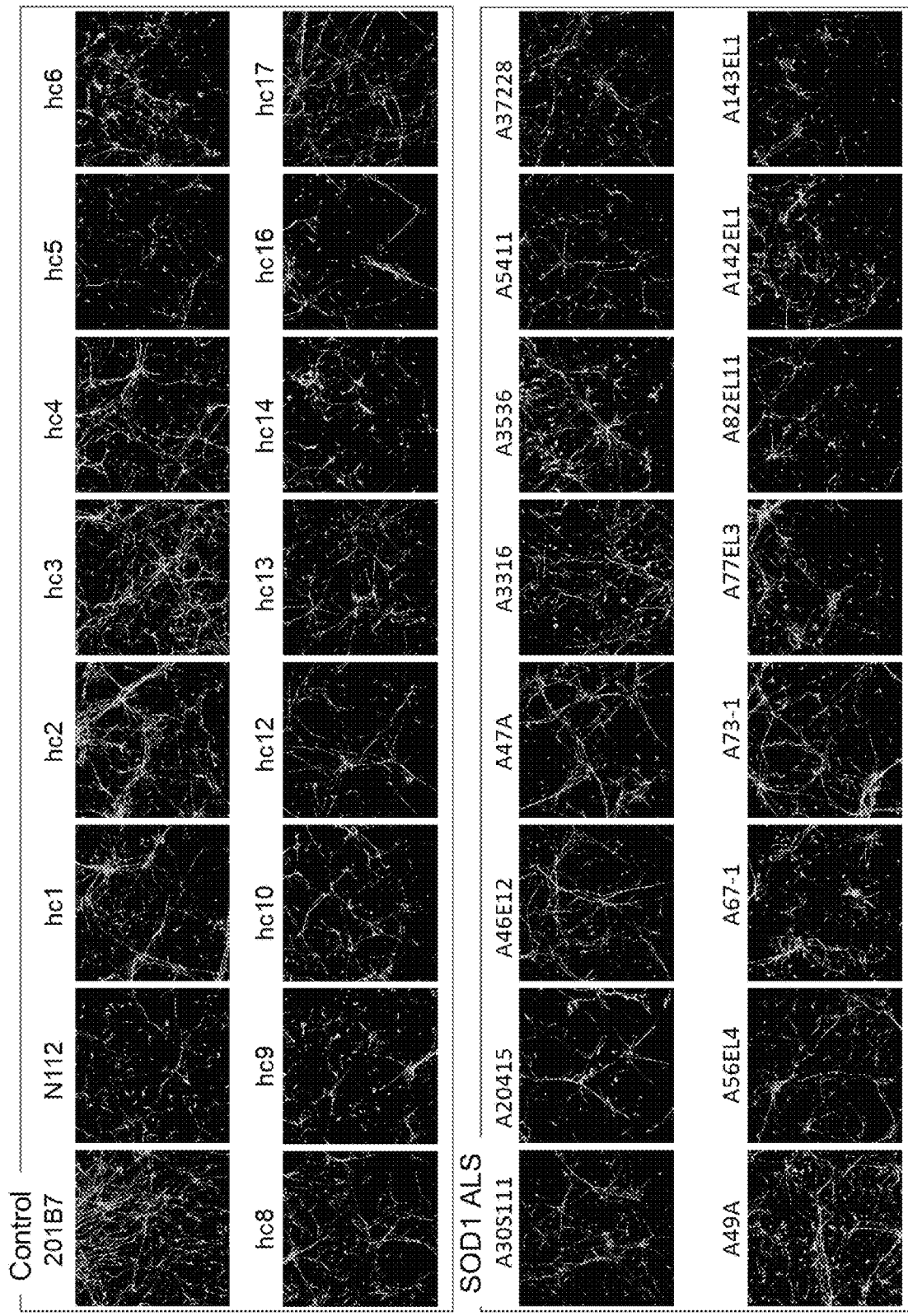
FIG. 9 is a view illustrating an example of a cell image.

FIG. 9 is a view illustrating an example of a cell image. The sixteen cell images included in the category "Control" illustrated in the drawing are images obtained by imaging the spinal motoneurons prepared from the iPS cells derived from sixteen healthy subjects. The sixteen cell images included in the category "SOD1 ALS" are images obtained by imaging the spinal motoneurons prepared from the iPS cells derived from sixteen ALS patients with SOD1 mutations. Each cell image is obtained by imaging the spinal motoneurons that was fixed with PFA and then stained with antibodies against neurofilament H which is a skeletal protein of nerve cells.

Experiment Example 2

(Training, Validation, Testing)
The prediction model MDL was trained using 225 images per iPS cell strain from sixteen healthy subjects and sixteen ALS patients, respectively, as training data. The program used as the prediction model MDL was VGG16 of Tensorflow/Keras.

Figure 10:
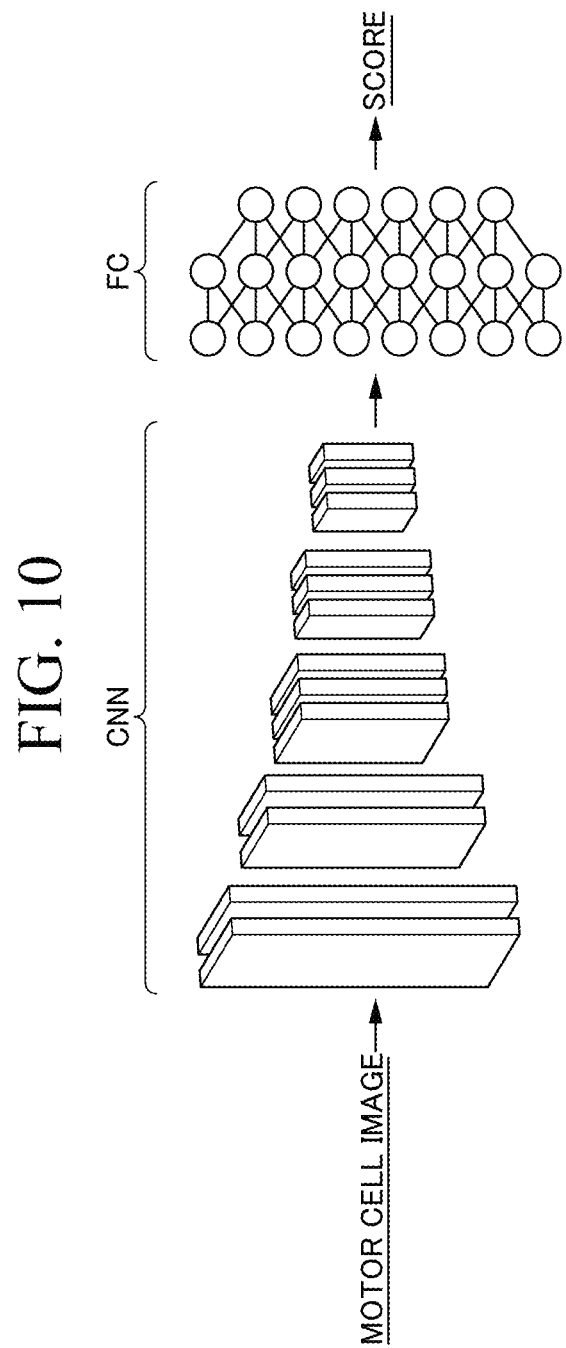
FIG. 10 is a view illustrating an example of the prediction model using Tensorflow/Keras.

FIG. 10 is a view illustrating an example of the prediction model MDL using Tensorflow/Keras. As illustrated in the drawing, the prediction model MDL is a neural network that includes thirteen convolutional layers (CNN in the drawing) and three fully-connected layers (FC in the drawing). The prediction model MDL was trained using a total of 5,400 images of motoneurons derived from twelve healthy subjects and twelve ALS patients as training data, and the validation of prediction accuracy was performed using a total of 1,350 images of motoneurons derived from another three healthy subjects and twelve ALS patients. Accordingly, the optimal parameters were set, and further, another healthy subjects and ALS patients were identified. As a result, the diagnostic results that showed high accuracy values for motoneuron images of healthy subjects and motoneuron images of ALS patients were obtained. Furthermore, it is possible to distinguish the images of motoneurons derived from the iPS cells of ALS patients and the images of motoneurons derived from the iPS cells to which gene restoration of the same person was performed, with high accuracy values.

Experiment Example 3

Figure 11:
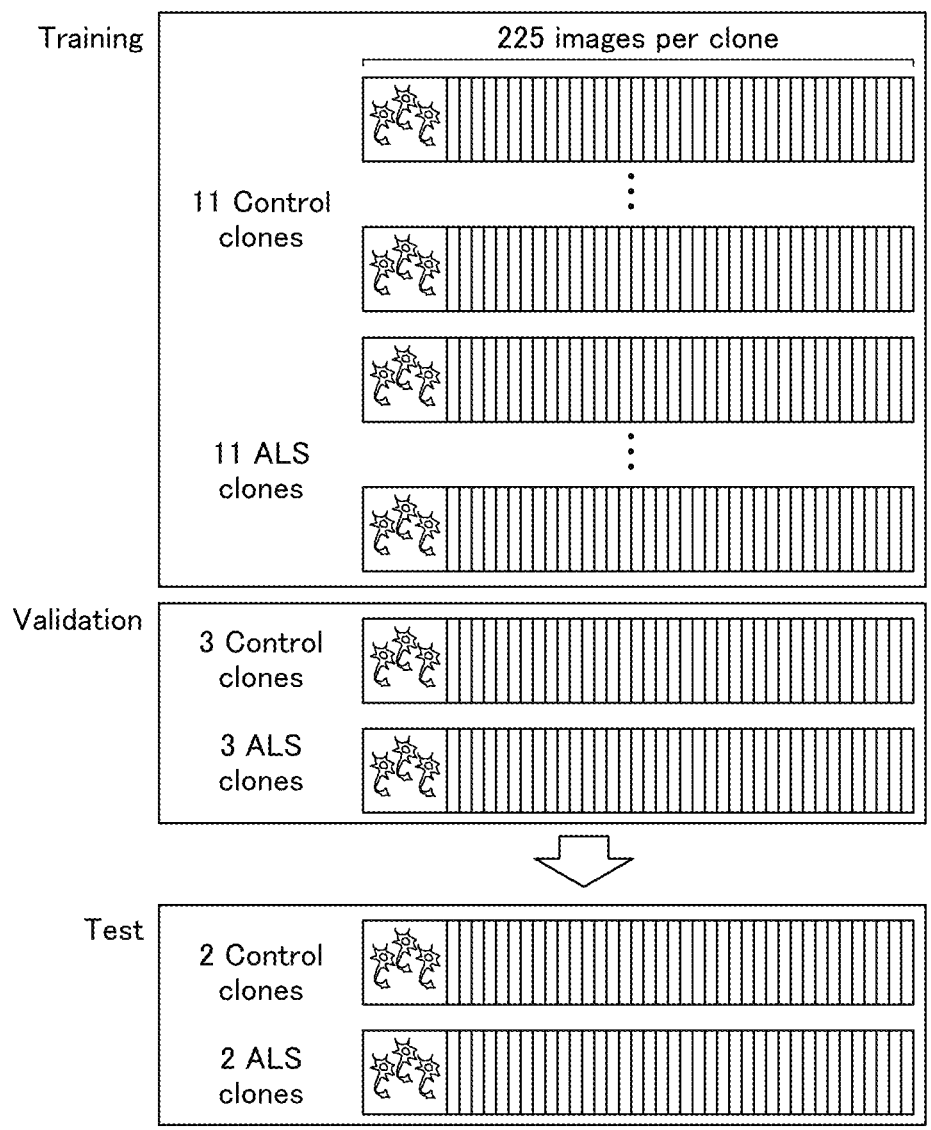
FIG. 11 is a view showing Experiment Example 3.

FIG. 11 is a view showing Experiment Example 3. As illustrated in FIG. 11, in Experiment Example 3, sixteen strains of motoneurons were first prepared by differentiation induction of each of the iPS cells of sixteen healthy subjects, and sixteen strains of motoneurons were prepared by differentiation induction of each of the iPS cells of sixteen ALS patients with SOD1 mutations. Hereinafter, the motoneurons prepared from the iPS cells derived from healthy subjects will be referred to as "healthy control clones", and the motoneurons prepared from the iPS cells derived from ALS patients will be referred to as "ALS clones".

Then, among the sixteen strains of healthy control clones, eleven strains were selected for training, three strains were selected for validation, and two strains were selected for testing. Similarly, among the sixteen ALS clones, eleven strains were selected for training, three strains were selected for validation, and two strains were selected for testing.

The prediction model MDL has been trained such that it is possible to identify a healthy subject and an ALS patient based on the motoneuron images by using images of eleven strains of healthy control clones for training, images of eleven strains of ALS clones for training, images of three strains of healthy control clones for validation, and images of three strains of ALS clones for validation. The number of images for each clone (motoneuron) was set to 225 per strain of motoneuron. Then, by using the sufficiently trained prediction model MDL, the prediction model MDL was tested using the images of two strains of healthy control clones derived from healthy subjects and two strains of ALS clones derived from ALS patients, which had been selected for testing.

Figure 12:
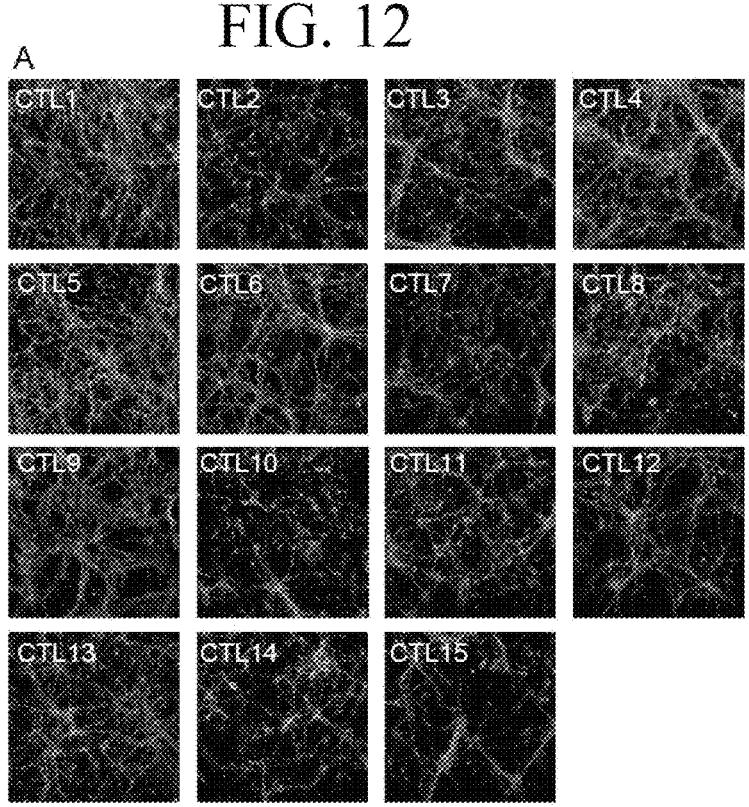
FIG. 12 is a view illustrating an example of a motor neuron image used as a healthy control clonal strain.
Figure 13:
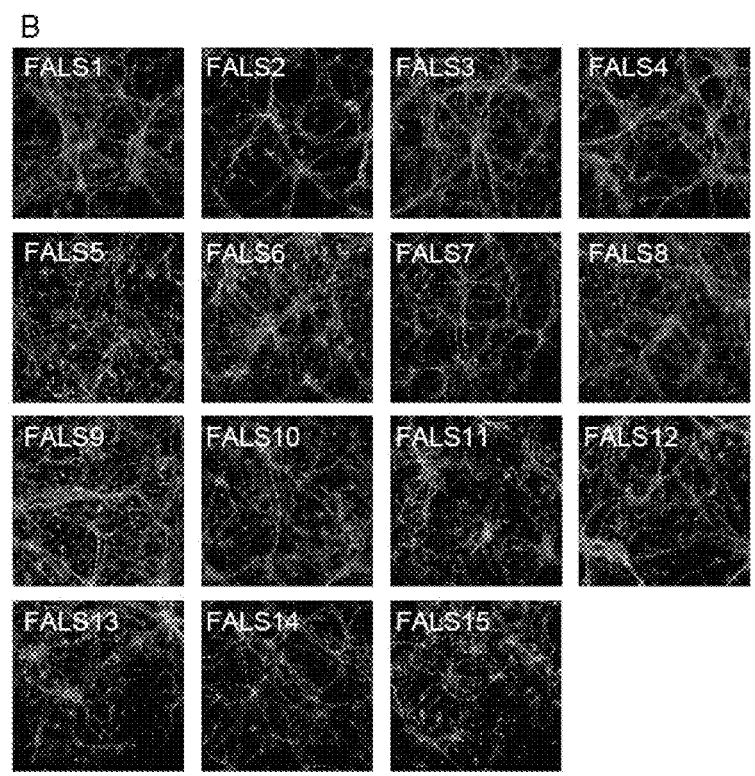
FIG. 13 is a view illustrating an example of a motoneuron image used as an ALS clonal strain.

FIG. 12 is a view illustrating an example of the motoneuron image used as a healthy control clonal strain, and FIG. 13 is a view illustrating an example of the motoneuron image used as the ALS clonal strain.

Figure 14:
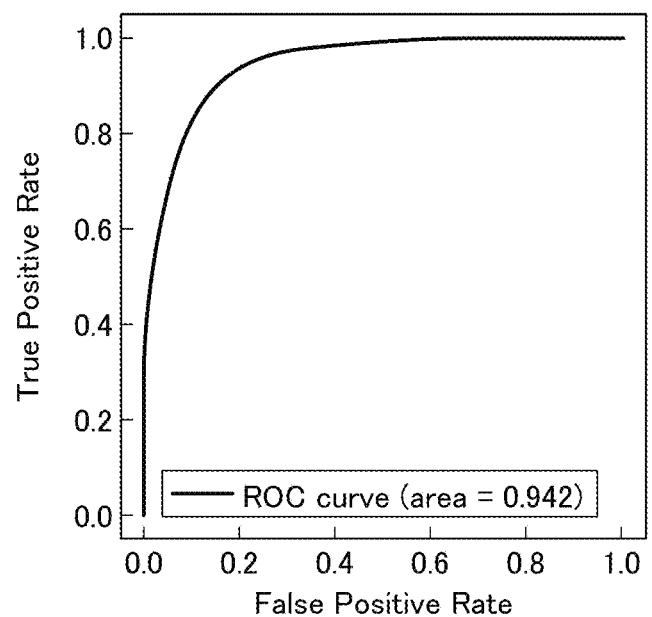
FIG. 14 is a view illustrating an example of a test result of the prediction model.

FIG. 14 is a view illustrating an example of a test result of the prediction model MDL. The horizontal axis in the drawing represents the false positive rate, and the vertical axis represents the true positive rate. As illustrated in the drawing, in a case where a receiver operating characteristic (ROC) curve was obtained, an area under the curve (AUC), which is the area under the ROC curve, was 0.942, indicating that ALS could be diagnosed with sufficient accuracy.

Figure 15:
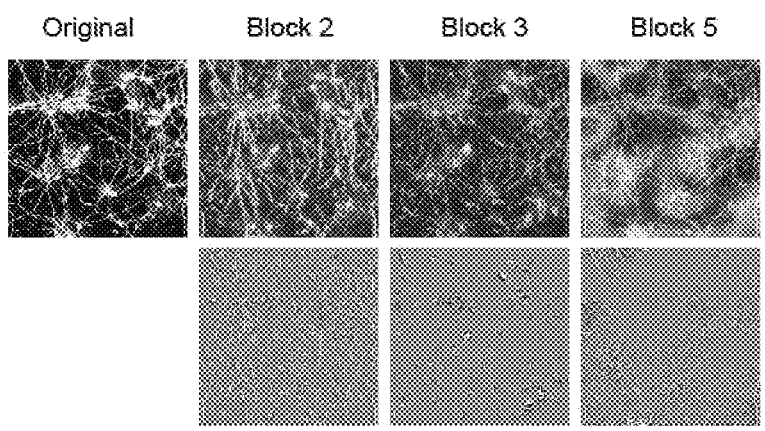
FIG. 15 is a view illustrating an example of image identification results of the prediction model.

FIG. 15 is a view illustrating an example of image identification results by the prediction model MDL. In the example illustrated in the drawing, it was visualized where in the image the prediction model MDL implemented by the CNN is being identified using gradient-weighted class activation mapping (Grad-CAM). This means that, according to Grad-CAM, the prediction model MDL focuses on characteristic parts such as cell bodies and neurites of motoneurons.

Figure 16:
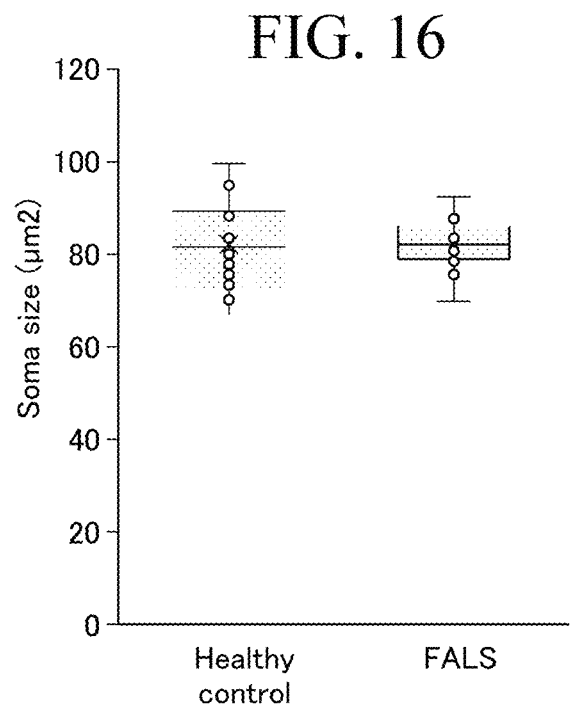
FIG. 16 is a view illustrating comparison results of areas of cell bodies of a healthy control clone and an ALS clone.
Figure 17:
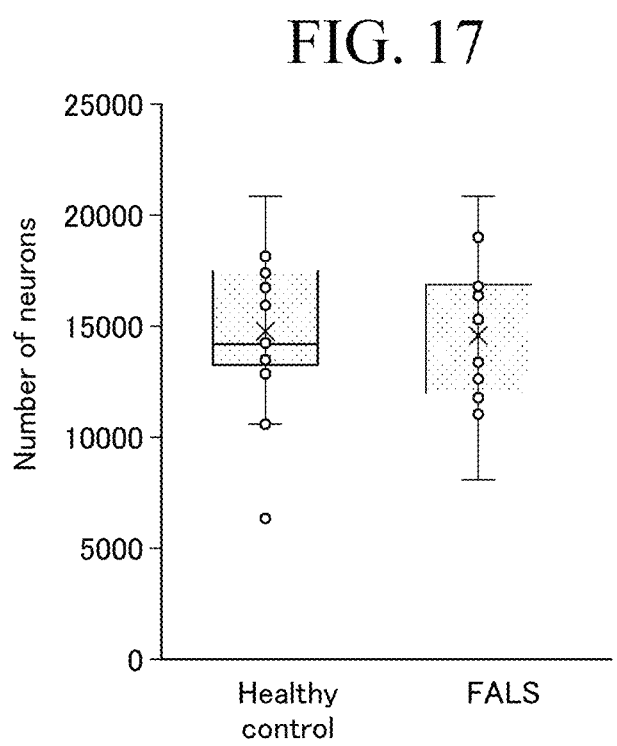
FIG. 17 is a view illustrating comparison results of the number of cells of the healthy control clone and the ALS clone.

FIG. 16 is a view illustrating comparison results of areas of cell bodies of a healthy control clone and an ALS clone. FIG. 17 is a view illustrating comparison results of the number of cells of the healthy control clone and the ALS clone. Using image analysis software, the area of cell bodies and the number of cells in the images are investigated, and no difference was found between the healthy control clones and the ALS clones.

Experiment Example 4

In Experiment Example 4, similar to Experiment Example 3, sixteen strains of motoneurons were first prepared by differentiation induction of each of the iPS cells of sixteen healthy subjects, and sixteen strains of motoneurons were prepared by differentiation induction of each of the iPS cells of sixteen sporadic ALS patients.

Then, among the sixteen strains of healthy control clones, which are motoneurons prepared from the iPS cells derived from the healthy subjects, eleven strains were selected for training, three strains were selected for validation, and two strains were selected for testing. Similarly, among the sixteen strains of ALS clones, which are motoneurons prepared from the iPS cells derived from the sporadic ALS patients, eleven strains were selected for training, three strains were selected for validation, and two strains were selected for testing.

The prediction model MDL has been trained such that it is possible to identify the healthy subject and the sporadic ALS patient based on the motoneuron images by using images of eleven strains of healthy control clones for training, images of eleven strains of ALS clones for training, images of three strains of healthy control clones for validation, and images of three strains of ALS clones for validation. The number of images for each clone (motoneuron) was set to 225 per strain of motoneuron. Then, by using the sufficiently trained prediction model MDL, the prediction model MDL was tested using the images of two strains of healthy control clones derived from healthy subjects and two strains of sporadic ALS clones derived from ALS patients, which had been selected for testing.

Figure 18:
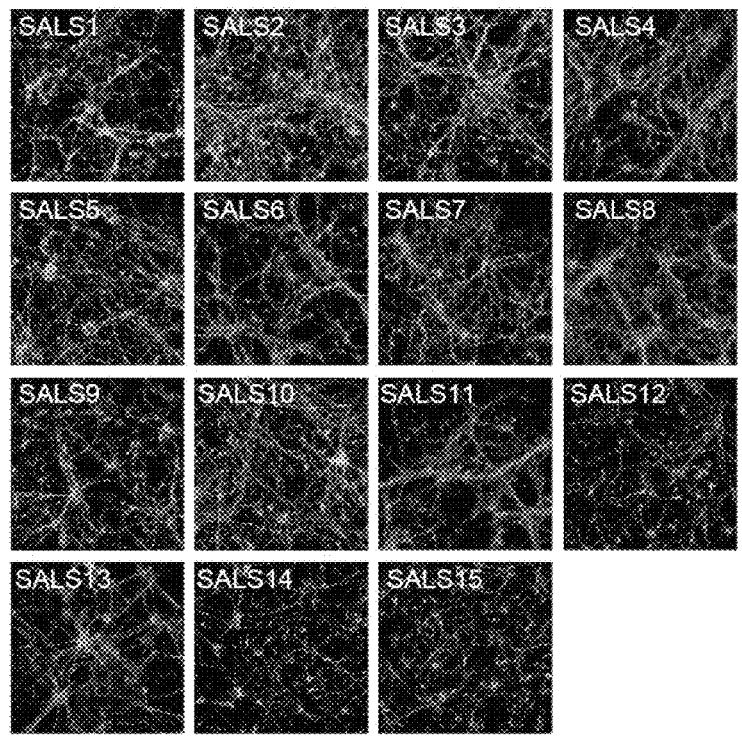
FIG. 18 is a view illustrating an example of a motoneuron image used as a sporadic ALS clonal strain.

FIG. 18 is a view illustrating an example of a motoneuron image used as a sporadic ALS clonal strain.

Figure 19:
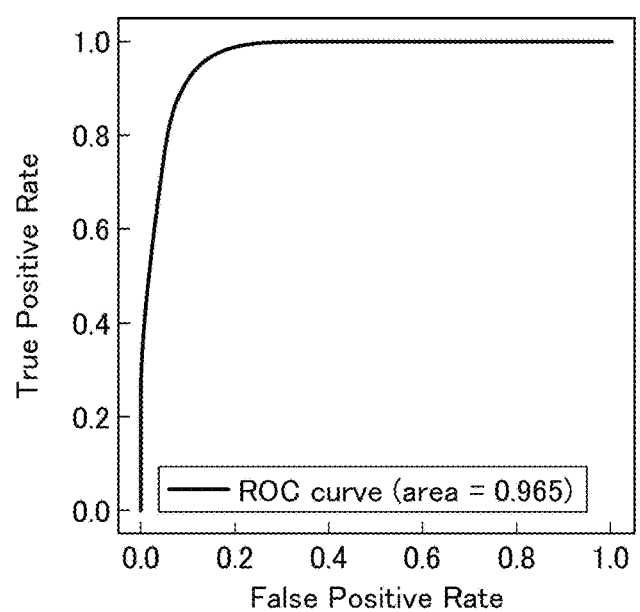
FIG. 19 is a view illustrating another example of a test result of the prediction model.

FIG. 19 is a view illustrating another example of a test result of the prediction model MDL. Similar to FIG. 14, the horizontal axis of FIG. 19 represents the false positive rate, and the vertical axis represents the true positive rate. As illustrated in the drawing, in a case where the ROC curve was calculated, the AUC, which is the area under the ROC curve, was 0.965, indicating that sporadic ALS could be diagnosed with sufficient accuracy.

Figure 20:
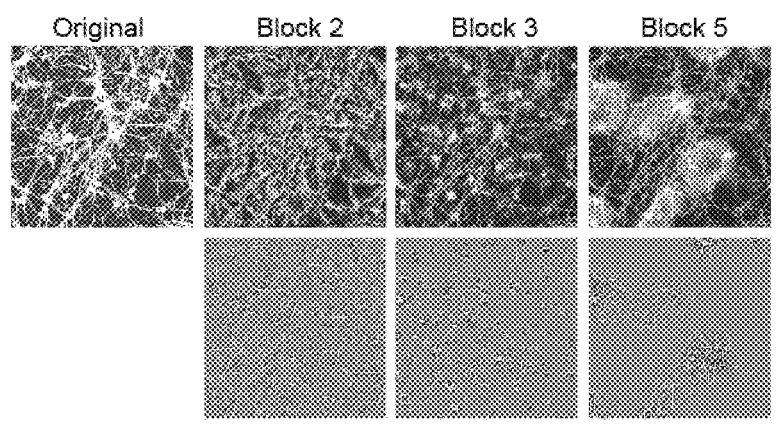
FIG. 20 is a view illustrating another example of image identification results by the prediction model.

FIG. 20 is a view illustrating another example of image identification results by the prediction model MDL. Similar to FIG. 15, in the example in FIG. 20, it was visualized where in the image the prediction model MDL implemented by the CNN is being identified using the Grad-CAM. This means that, according to Grad-CAM, the prediction model MDL focuses on characteristic parts such as cell bodies and neurites of motoneurons.

The invention claimed is:

1. An information processing device comprising:
a processor configured to:
acquire images obtained by imaging cells differentiated from pluripotent stem cells derived from a subject;
input the acquired images to a neural network trained on training data in which information indicating at least a phenotype of a neurological disease is associated with an image obtained by imaging cells of the neurological disease differentiated from the pluripotent stem cells; and
predict an onset of the neurological disease of the subject based on the information indicating the phenotype output by the neural network in response to the acquired images input,
wherein:
the training data used for training the neural network is data in which age at the onset of the neurological disease is further associated with the image obtained by imaging the cells of the neurological disease,
the neural network outputs the age when the acquired images obtained by imaging the cells are input, and
the processor being further configured to predict a time period until the onset of the neurological disease of the subject based on the age output by the neural network.

2. The information processing device according to claim 1, wherein:
the training data used for training the neural network is data in which a symptomatic period of the neurological disease is further associated with the image obtained by imaging the cells of the neurological disease,
the neural network outputs the symptomatic period when the acquired images obtained by imaging the cells are input, and
the processor being further configured to predict a progression rate of the neurological disease that the subject develops based on the symptomatic period output by the neural network.

3. The information processing device according to claim 1, wherein:
the training data used for training the neural network further includes data in which information indicating that a cell does not show the phenotype of the neurological disease is associated with the image obtained by imaging the cells differentiated from the pluripotent stem cells derived from a healthy subject.

4. The information processing device according to claim 1, wherein:
the training data used for training the neural network further includes, in addition to the images obtained by imaging the cells of the neurological disease, data in which information indicating the phenotype of the neurological disease is associated with personal information indicating the sex and presence or absence of genetic polymorphism or a specific gene of the patient with the neurological disease,
the processor being further configured to:
acquire personal information on the sex and the presence or absence of genetic polymorphism or a specific gene of the subject,
input the acquired images and the acquired personal information to the neural network, and
predict the onset of the neurological disease of the subject based on the information indicating the phenotype output by the neural network in response to the acquired images and the acquired personal information input.

5. The information processing device according to claim 1, the processor being further configured to train the neural network based on the training data.

6. The information processing device according to claim 1, wherein:
the cells differentiated from the pluripotent stem cells are nerve cells, glial cells, vascular endothelial cells, pericytes, choroid plexus cells, or immune system cells.

7. The information processing device according to claim 1,
wherein the neurological disease includes at least one of amyotrophic lateral sclerosis (ALS), Alzheimer's disease, Parkinson's disease, spinocerebellar degeneration, frontotemporal lobar degeneration, Lewy body dementia, multiple system atrophy, Huntington's disease, progressive supranuclear palsy, or Corticobasal degeneration.

8. An information processing method performed by a computer, the method comprising:
acquiring images obtained by imaging cells differentiated from pluripotent stem cells derived from a subject,
inputting the acquired images to a neural network trained on training data in which information indicating at least a phenotype of a neurological disease is associated with an image obtained by imaging the cells of the neurological disease differentiated from the pluripotent stem cells, and
predicting an onset of the neurological disease of the subject based on the information indicating the phenotype output by the neural network in response to the acquired images input,
wherein:
the training data used for training the neural network is data in which age at the onset of the neurological disease is further associated with the image obtained by imaging the cells of the neurological disease,
the neural network outputs the age when the acquired images obtained by imaging the cells are input, and
the method further comprising predicting a time period until the onset of the neurological disease of the subject based on the age output by the neural network.

9. A computer-readable non-transitory storage medium storing a program causing a computer to execute instructions, the instructions including:
acquiring images obtained by imaging cells differentiated from pluripotent stem cells derived from a subject,
inputting the acquired images to a neural network trained on training data in which information indicating at least a phenotype of a neurological disease is associated with an image obtained by imaging the cells of the neurological disease differentiated from the pluripotent stem cells, and
predicting an onset of the neurological disease of the subject based on the information indicating the phenotype output by the neural network in response to the acquired images input,
wherein:
the training data used for training the neural network is data in which age at the onset of the neurological disease is further associated with the image obtained by imaging the cells of the neurological disease,
the neural network outputs the age when the acquired images obtained by imaging the cells are input, and
the instructions further including predicting a time period until the onset of the neurological disease of the subject based on the age output by the neural network.

10. An information processing device comprising:
a processor configured to:
acquire images obtained by imaging cells differentiated from pluripotent stem cells derived from a subject;
input the acquired images to a neural network trained on training data in which information indicating at least a phenotype of a neurological disease is associated with an image obtained by imaging cells of the neurological disease differentiated from the pluripotent stem cells; and
predict an onset of the neurological disease of the subject based on the information indicating the phenotype output by the neural network in response to the acquired images input,
wherein:
the training data used for training the neural network is data in which a symptomatic period of the neurological disease is further associated with the image obtained by imaging the cells of the neurological disease,
the neural network outputs the symptomatic period when the acquired images obtained by imaging the cells are input, and
the processor being further configured to predict a progression rate of the neurological disease that the subject develops based on the symptomatic period output by the neural network.

11. An information processing device comprising:
a processor configured to:
acquire images obtained by imaging cells differentiated from pluripotent stem cells derived from a subject;
input the acquired images to a neural network trained on training data in which information indicating at least a phenotype of a neurological disease is associated with an image obtained by imaging cells of the neurological disease differentiated from the pluripotent stem cells; and
predict an onset of the neurological disease of the subject based on the information indicating the phenotype output by the neural network in response to the acquired images input,
wherein:
the training data used for training the neural network further includes, in addition to the images obtained by imaging the cells of the neurological disease, data in which information indicating the phenotype of the neurological disease is associated with personal information indicating the sex and presence or absence of genetic polymorphism or a specific gene of the patient with the neurological disease,
the processor being further configured to:
acquire personal information on the sex and the presence or absence of genetic polymorphism or a specific gene of the subject,
input the acquired images and the acquired personal information to the neural network, and
predict the onset of the neurological disease of the subject based on the information indicating the phenotype output by the neural network in response to the acquired images and the acquired personal information input.

12. An information processing method performed by a computer, the method comprising:
acquiring images obtained by imaging cells differentiated from pluripotent stem cells derived from a subject,
inputting the acquired images to a neural network trained on training data in which information indicating at least a phenotype of a neurological disease is associated with an image obtained by imaging the cells of the neurological disease differentiated from the pluripotent stem cells, and
predicting an onset of the neurological disease of the subject based on the information indicating the phenotype output by the neural network in response to the acquired images input, wherein:
the training data used for training the neural network is data in which a symptomatic period of the neurological disease is further associated with the image obtained by imaging the cells of the neurological disease,
the neural network outputs the symptomatic period when the acquired images obtained by imaging the cells are input, and
the method further comprising predicting a progression rate of the neurological disease that the subject develops based on the symptomatic period output by the neural network.

13. An information processing method performed by a computer, the method comprising:
acquiring images obtained by imaging cells differentiated from pluripotent stem cells derived from a subject,
inputting the acquired images to a neural network trained on training data in which information indicating at least a phenotype of a neurological disease is associated with an image obtained by imaging the cells of the neurological disease differentiated from the pluripotent stem cells, and
predicting an onset of the neurological disease of the subject based on the information indicating the phenotype output by the neural network in response to the acquired images input,
wherein:
the training data used for training the neural network further includes, in addition to the images obtained by imaging the cells of the neurological disease, data in which information indicating the phenotype of the neurological disease is associated with personal information indicating the sex and presence or absence of genetic polymorphism or a specific gene of the patient with the neurological disease,
the method further comprising:
acquiring personal information on the sex and the presence or absence of genetic polymorphism or a specific gene of the subject,
inputting the acquired images and the acquired personal information to the neural network, and
predicting the onset of the neurological disease of the subject based on the information indicating the phenotype output by the neural network in response to the acquired images and the acquired personal information input.

14. A computer-readable non-transitory storage medium storing a program causing a computer to execute instructions, the instructions including:
acquiring images obtained by imaging cells differentiated from pluripotent stem cells derived from a subject,
inputting the acquired images to a neural network trained on training data in which information indicating at least a phenotype of a neurological disease is associated with an image obtained by imaging the cells of the neurological disease differentiated from the pluripotent stem cells, and
predicting an onset of the neurological disease of the subject based on the information indicating the phenotype output by the neural network in response to the acquired images input,
wherein:
the training data used for training the neural network is data in which a symptomatic period of the neurological disease is further associated with the image obtained by imaging the cells of the neurological disease,
the neural network outputs the symptomatic period when the acquired images obtained by imaging the cells are input, and
the instructions further including predicting a progression rate of the neurological disease that the subject develops based on the symptomatic period output by the neural network.

15. A computer-readable non-transitory storage medium storing a program causing a computer to execute instructions, the instructions including:
acquiring images obtained by imaging cells differentiated from pluripotent stem cells derived from a subject,
inputting the acquired images to a neural network trained on training data in which information indicating at least a phenotype of a neurological disease is associated with an image obtained by imaging the cells of the neurological disease differentiated from the pluripotent stem cells, and
predicting an onset of the neurological disease of the subject based on the information indicating the phenotype output by the neural network in response to the acquired images input,
wherein:
the training data used for training the neural network further includes, in addition to the images obtained by imaging the cells of the neurological disease, data in which information indicating the phenotype of the neurological disease is associated with personal information indicating the sex and presence or absence of genetic polymorphism or a specific gene of the patient with the neurological disease,
the instructions further including:
acquiring personal information on the sex and the presence or absence of genetic polymorphism or a specific gene of the subject,
inputting the acquired images and the acquired personal information to the neural network, and
predicting the onset of the neurological disease of the subject based on the information indicating the phenotype output by the neural network in response to the acquired images and the acquired personal information input.

* * * * *